United States Patent [19]
Broadbent

[11] 4,049,460
[45] Sept. 20, 1977

[54] ROACH BAIT COMPOSITION
[75] Inventor: David J. Broadbent, Racine, Wis.
[73] Assignee: S. C. Johnson & Son, Inc., Racine, Wis.
[21] Appl. No.: 670,477
[22] Filed: Mar. 25, 1976
[51] Int. Cl.² ............................................. A01N 17/14
[52] U.S. Cl. ................................. 106/15 R; 106/162; 106/272; 424/84; 424/200; 426/1
[58] Field of Search ...................... 106/15 R, 162, 272; 424/84, 200; 426/1

[56] References Cited
U.S. PATENT DOCUMENTS
| | | | |
|---|---|---|---|
| 3,162,575 | 12/1964 | Lang | 424/84 |
| 3,244,586 | 5/1966 | Rigterink | 424/200 |

FOREIGN PATENT DOCUMENTS
| | | | |
|---|---|---|---|
| 4,723,198 | 6/1972 | Japan | 424/84 |
| 440,921 | 1/1936 | United Kingdom | 424/84 |

Primary Examiner—Lorenzo B. Hayes

[57] ABSTRACT

An insecticidal roach bait which is particularly preferred by roaches, including American and German roaches, comprising from about 20–54.75% by weight of a non-repellent binder, from about 79.75–45% by weight of a food attractant selected from dry dog food, maltose, brown sugar, and mixtures thereof, and from about 0.25–5% by weight of 0,0-diethyl-0-(3,5,6-trichloro-2-pyridyl) phosphorothioate.

10 Claims, No Drawings

ROACH BAIT COMPOSITION

BRIEF DESCRIPTION AND BACKGROUND OF THE INVENTION

This invention relates to a bait for cockroaches. More particularly, this invention relates to a bait for cockroaches containing a toxicant.

The cockroach is one of the oldest pests known to mankind. Efforts have been made continually over the years to effectively control roach populations in homes, warehouses, business establishments, etc. Control and eradication of the roach population is most difficult because of the feeding habits of cockroaches. Cockroaches generally are nocturnal creatures which explore primarily out of hunger. This exploration is influenced by temperature, humidity, and light among other factors. Roaches breed at a high rate and, accordingly, complete eradication of this noxious pest is most difficult. However, control has been achieved using various methods. Most of these prior art methods involve the use of residual insecticide sprays and/or the placing of various bait compositions.

Residual sprays, although effective for a reasonable length of time on many surfaces are not effective on certain surfaces. For instance, a spray which is quite effective on a sealed surface, such as stainless steel or ceramic tile, may not be effective when used on an unsealed surface, such as unpainted wood or unsealed tile.

Prior art baits, such as those using boric acid, arsenic, Baygon, and other toxicants, have also not been particularly effective since these baits are somewhat messy to use and do not offer a relatively high kill rate.

Effective studies have been done in the preparation of baits for cockroaches. Two articles disclose the incorporation of preformed Kepone (decachlorooctahydro-1,3,4-metheno-2H-cyclobuta [cd] pentalen-2-one) bait pellets in paraffin. These Kepone pellets are 0.125% Kepone impregnated in corn husks or grain. The Eversole article, page 1316 of *THE JOURNAL OF ECONOMIC ENTOMOLOGY,* Vol. 64, No. 5, does not disclose any particular ratio of bait pellets to paraffin, but it is apparent from the method described in this article that a high percentage of paraffin to bait is utilized. Likewise, an article in Vol. 66, No. 6, pages 1277-1278, in *THE JOURNAL OF ECONOMIC ENTOMOLOGY,* the baits were prepared having 1.2 parts of bait to 1 part paraffin. Lastly, a paper published by M. D. Miesch, Jr., in 1969 by University Microfilms, Ann Arbor, Michigan, entitled "Ecological and Phisiological Mechanisms Influencing Food Finding in Blattaria" indicates on page 65 that dog chows may be good baits when compared to potato flakes which are a standard bait. It is clear from the disclosure in these articles that the paraffin is designed to protect the bait from the adverse effects of humidity and temperature found in the environment wherein the baits were to be placed, i.e., sewer lines.

It has, therefore, been found that a highly effective and attractive cockroach bait can be prepared by intimately mixing from about 20-54.75% by weight of a non-repellent binder, from about 79.75-45% by weight of dry dog food and maltose, brown sugar, or mixtures thereof, and from about 0.25-5% by weight 0-0-diethyl-0-(3,5,6-trichloro-2-pyridyl) phosphorothioate. The above compositions are especially attractive to roaches and in fact are preferred by roaches over their normal daily diet. When formed into appropriate sized bait pellets and placed in an appropriate concentration, the use of the bait of the present invention effectively controls roaches for a reasonable length of time. Further, the use of the baits of the present invention controls the hatch of eggs providing further effective control.

OBJECTS AND ADVANTAGES OF THE INVENTION

It is, therefore, the primary object of the present invention to prepare a roach bait composition which is highly effective, yet convenient to use.

It is a further object of the present invention to provide a roach bait which is especially attractive to roaches.

It is a still further object of the present invention to provide a roach bait composition which has no repellency characteristics and which is more attractive to the roaches than a normal diet.

It is a still further object of the present invention to provide a roach bait which exhibits systemic action by preventing eggs from hatching.

Still further objects and advantages of the bait of the present invention will become more apparent from the following detailed description thereof.

DETAILED DESCRIPTION OF THE INVENTION AND PREFERRED EMBODIMENTS

The bait of the present invention comprises from about 20-54.75% by weight and preferably 25-39.75% by weight of a nonrepellent binder, from about 79.75-45% by weight and preferably 79.75-55% by weight of a food attractant selected from dry dog food, maltose, brown sugar, and mixtures thereof, and from about 0.25-5% by weight and preferably 0.25-2% by weight of 0,0-diethyl-0-(3,5,6-trichloro-2-pyridyl) phosphorothioate.

The most preferred compositions comprise from 24-34.5% by weight of a wax, 65-75% by weight of a food attractant material, and 0.5-1% by weight of an insecticide.

The binders used in the present invention may be any material capable of giving the bait composition sufficient cohesiveness so the same may be formed into conveniently shaped blocks, pellets, etc. These binders must not be inherently repellent to cockroaches. Suitable binders include various natural and synthetic waxes, carboxymethyl cellulose, starches, etc. As disclosed in the Eversole and Wright et al articles cited above, cockroaches will eat through waxy materials to reach a bait material. Waxes are the preferred binders for use in the present invention. Suitable waxes include paraffin waxes melting between 100°-250° F., microcrystalline waxes, polyethylene waxes, beeswax, and certain other natural waxes. The primary criterion is that the wax or other binder be sufficiently hard to hold the bait in place at room temperature yet have a sufficiently low melting point so that the same can be processed into the bait pellets or tablets. Certain natural waxes, however, cannot be used such as lemon wax which exhibits a repellent response in roaches. The baits of the present invention can comprise from about 20-54.75% by weight binder, preferably from about 23.-39.75% by weight binder, and most preferably from about 25-35% by weight binder.

The food attractant, or bait portion of the bait of the present invention, comprises dry dog food, maltose, brown sugar, or mixtures. When used in the instant specification and claims, the term "dry dog food" means a dry food for dogs containing a minimum of 15.0% protein, a minimum of 5% fat, between 5 and 15% moisture, and a maximum of 10% fiber formed from some or all of the following ingredients: meat and bone meal, wheat germ meal, ground oats, ground yellow corn, ground grain sorghums, wheat middlings, ground wheat, soybean meal, cereal food fibers, dried whey, animal fats, brewer's dried yeast, vitamins, minerals and preservatives. Dry dog foods may be expanded with air or unexpanded. Commercially available dry dog foods include Purina Dog Chow, Gravy Train, Purina Dog Meal, Friskies, etc. Brown sugars are primarly sucrose crystals which have been coated with a refined dark syrup. The food attractant portion of the cockroach bait of the present invention comprises from about 79.25–45% by weight, and preferably from about 75–45% by weight, and most preferably from about 65–75% by weight of the total bait composition. The preferred material is Purina Dog Chow, an expanded dry dog food with a minimum of 23% protein, a minimum of 8.0% fat, and a maximum fiber content of 4.5%, either alone or mixed with small quantities of maltose.

The baits of the present invention also contain from about 0.25–5% by weight, and preferably from about 0.25–2% by weight and most preferably 0.5–1.0% by weight of 0,0-diethyl-0-(3,5,6-trichloro-2-pyridyl) phosphorothioate, also known as Dursban. These insecticides are most effective and offer a relatively high LT 84, the time to kill 84% of the roaches. The above toxicant is not repellent to roaches and, although there are strains of roaches resistant to many insecticides, there are no strains of Dursban-resistant roaches currently known. Furthermore, Dursban, which is the preferred insecticide, offers a lethal Lt 84 of 8 hours, a very quick and very high percent mortality. Also, Dursban appears to offer the further feature of having some residual or systemic kill, i.e., adult females which have eaten the bait lay egg cases which do not fully develop. Accordingly, Dursban is the preferred toxicant for use in the baits of the present invention.

The baits of the present invention will now be illustrated by the following examples which are for the purpose of illustration only. In these examples, all parts and percentages are by weight and all temperatures are in degrees Centigrade.

EXAMPLE 1

Some 69.5 grams of Purina Dog Chow are mixed with 30 grams of paraffin wax having a melt point of 120° F. and 0.5 grams of 0,0-diethyl-0-(3,5,6-trichloro-2-pyridyl) phosphorothioate (Dursban) at about 125° F. until the Dog Chow, wax, and Dursban are intimately mixed. This mixture is then extended into 5 gram cylindrical bait pellets. Some 25 adult male cockroaches are placed in a 7⅞ × 10⅜ × 3¾ plastic tray with lab roach food, water, and a roach hide. After the roaches have been given 24 hours to become acclimated to the tray, one 5-gram bait pellet is placed in the tray. The percent mortality is calculated and the results are shown in Table I.

EXAMPLES 2–9 AND COMPARATIVE EXAMPLE 1

Example 1 is repeated except the Dursban concentration ratio is changed as shown in Table I with a consistent change in wax content.

TABLE I

| Example | % Dursban | 1 | 2 | 4 | 6 | 8 | 24 | 32 | 48 | 72 | 96 |
|---|---|---|---|---|---|---|---|---|---|---|---|
| 2 | 0.10 | 0 | — | 12 | — | 67 | 89 | 90 | 90 | 97 | 100 |
| 3 | 0.25 | — | 1 | 42 | 72 | 81 | 92 | — | 100 | — | — |
| 4 | 0.35 | — | 3 | 67 | 85 | 90 | 93 | — | 100 | — | — |
| 1 | 0.50 | — | 8 | 68 | 83 | 90 | 98 | — | 100 | — | — |
| 5 | 0.75 | — | 25 | 83 | 89 | 89 | 98 | — | 100 | — | — |
| 6 | 1.00 | — | 22 | 87 | 93 | 96 | 100 | — | 100 | — | — |
| 7 | 1.25 | — | 24 | 88 | 98 | 99 | 100 | — | 100 | — | — |
| 8 | 1.50 | — | 40 | 93 | 99 | 100 | 100 | — | 100 | — | — |
| CE 1 | 0.05 | 0 | — | 3 | — | 14 | 46 | 52 | 65 | 73 | 94 |

(Mortality % (hours))

As is apparent, even very low levels of toxicant are effective in controlling a roach population, if given sufficient time as the roaches continue to feed on the bait. To be considered effective, the bait must have a LT 84 of 72 hours or less.

EXAMPLES 9–12

Experiment 1 is repeated except the Purina Dog Chow is replaced with various other commercially available dry dog foods and Maltose as shown in Table II. The control is the composition of Example 1.

TABLE II

| Example | Bait | 1 | 4 | 8 | 24 | 32 | 48 | 72 | 96 |
|---|---|---|---|---|---|---|---|---|---|
| Control | Purina Dog Chow | 0 | 19 | 50 | 86 | 87 | 93 | 98 | 99 |
| 9 | Maltose | 0 | 47 | 75 | 88 | 89 | 92 | 98 | 100 |
| 10 | Gravy Train | 0 | 37 | 66 | 87 | 88 | 94 | 99 | 100 |
| 11 | Friskies | 0 | 35 | 62 | 82 | 84 | 90 | 97 | 99 |
| 12 | Purina Dog Meal | 0 | 30 | 52 | 80 | 81 | 90 | 96 | 90 |

(% Mortality (hours))

As is apparent, the particular dry dog food does not greatly affect the effectiveness of the bait.

EXAMPLES 13–22 AND COMPARATIVE EXAMPLES 2–3

Experiment 1 is repeated except the levels of Purina Dog Chow and wax are varied and microcrystalline wax is substituted for the paraffin as indicated in Table III.

TABLE III

| Ex. | % Dog Chow | % Paraffin | % Micro Wax | 2 | 4 | 6 | 8 | 24 | 48 |
|---|---|---|---|---|---|---|---|---|---|
| 13 | 89.5 | 10 | — | 6 | 45 | 65 | 71 | 88 | 96 |
| 14 | 79.5 | 20 | — | 22 | 62 | 74 | 80 | 92 | 96 |
| 15 | 74.5 | 25 | — | 69 | 92 | 96 | 96 | 100 | 100 |

(% Mortality (hours))

TABLE III-continued

| Ex. | % Dog Chow | % Paraffin | % Micro Wax | % Mortality (hours) | | | | | |
|---|---|---|---|---|---|---|---|---|---|
| | | | | 2 | 4 | 6 | 8 | 24 | 48 |
| 16 | 69.5 | 30 | — | 82 | 98 | 98 | 98 | 100 | 100 |
| 17 | 49.5 | 50 | — | 62 | 94 | 96 | 96 | 100 | 100 |
| CE-2 | 19.5 | 80 | — | 8 | 22 | 28 | 28 | 38 | 46 |
| 18 | 89.5 | — | 10 | 12 | 62 | 72 | 78 | 94 | 98 |
| 19 | 79.5 | — | 20 | 2 | 52 | 68 | 80 | 96 | 98 |
| 20 | 74.5 | — | 25 | 8 | 58 | 70 | 78 | 86 | 92 |
| 21 | 69.5 | — | 30 | 14 | 86 | 90 | 90 | 94 | 96 |
| 22 | 49.5 | — | 50 | 2 | 68 | 74 | 78 | 94 | 96 |
| CE-3 | 19.5 | — | 80 | 0 | 0 | 0 | 0 | 0 | 2 |

Small variations in the dry dog food and wax content do not greatly affect the performance. The paraffin wax does appear to be slightly preferred over the microcrystalline wax.

COMPARATIVE EXAMPLES 4-11

A number of commercially available roach baits were tested and compared to the bait of Example 1. The results are shown in Table IV which shows the toxicant and percent toxicant in each bait as well as the percent mortality.

TABLE IV

| Comp. Ex. | Toxicant | % Conc. | % Mortality (hours) | | | | | | | |
|---|---|---|---|---|---|---|---|---|---|---|
| | | | 1 | 4 | 8 | 24 | 32 | 48 | 72 | 96 |
| 4 | Baygon | 2.0 | 16 | 36 | 40 | 44 | 49 | 52 | 59 | 79 |
| 5 | Lead Arsenate | 16.2 | 0 | 0 | 0 | 1 | 4 | 10 | 11 | — |
| 6 | Kepone | 0.125 | 0 | 11 | 11 | 14 | 14 | 14 | 48 | 93 |
| 7 | Baygon | 2.0 | 13 | 57 | 65 | 74 | 76 | 81 | 87 | 94 |
| 8 | Borax | 50.0 | 0 | 0 | 0 | 1 | 1 | 1 | 2 | 2 |
| 9 | Boric Acid | 50.0 | 0 | 0 | 0 | 1 | 1 | 2 | 8 | 10 |
| 10 | Baygon | 2.0 | 4 | 5 | 8 | 18 | 18 | 21 | 25 | 28 |
| 11 | Baygon | 1.0 | 2 | 14 | 47 | 72 | 74 | 81 | 90 | 91 |
| Ex. 1 | Dursban | 0.5 | — | 68 | 90 | 98 | — | 100 | — | — |

Although some of the baits using Baygon had a relatively high kill percentage, at the first hour the rate was not as high as the present invention. Further, none of the commercial baits had 100% kill, even at 96 hours.

COMPARATIVE EXAMPLE 12

Kepone bait pellets were imbedded in paraffin as described in THE JOURNAL OF ECONOMIC ENTOMOLOGY, Vol. 66, No. 6, page 1277. These were compared to a bait prepared as in Example 1 in a side-by-side bioassy test. 100 adult male German roaches were placed in each tank and starved for 24 hours. The baits were then placed in the tanks. The results are shown in Table V.

TABLE V

| | % Toxicant | % Mortality (hours) | | | | | |
|---|---|---|---|---|---|---|---|
| | | 4 | 8 | 24 | 48 | 72 | 96 |
| Comparative Example 12 | 0.125 | 0 | 0 | 0 | 73 | 96 | 100 |
| Example 1 | 0.5 | 100 | 100 | 100 | 100 | 100 | 100 |

It is apparent the baits of the present invention are more effective over shorter periods of time. Kepone is slow acting and did give 100% kill after 96 hours in this test, but there was no alternate food source available.

EXAMPLE 23 and COMPARATIVE EXAMPLE 13

The bait of Example 1 and Comparative Example 12 are tested on roaches allowed to feed for a limited time. Twelve tanks containing 2 adult male German roaches were used for each test. The roaches were starved for 24 hours and then allowed to feed on the bait for 5 minutes. The bait is then removed and food is placed in the tank. The results are shown in Table VI.

TABLE VI

| | % Mortality (hours) | | | |
|---|---|---|---|---|
| | 24 | 48 | 72 | 96 |
| Example 23 | 83.3 | 83.3 | 83.3 | 83.3 |
| Comparative Example 13 | 0 | 0 | 0 | 0 |

Although complete kill was not achieved with the bait of the present invention, the differences are surprising and show that even a small quantity of the bait of the present invention is toxic to the roaches.

EXAMPLE 24 and COMPARATIVE EXAMPLE 14

The baits of Example 1 and Comparative Example 12 were tested for relative attractancy. One hundred adult male German cockroaches are placed in a tank and starved for 24 hours. A bait of Example 1 and a bait of Comparative Example 12 are each placed in a greased lucite ring trap inside the tank. Mortality and trapping counts are taken at 24 hours and are shown in Table VII.

TABLE VII

| | # Attracted | % Mortality of Attracted | % Attracted |
|---|---|---|---|
| Example 24 | 30 | 100 | 31.9 |
| Comparative Example 14 | 64 | 1.6 | 68.1 |

Although the Kepone bait is initially more attractive, the slow and uneffective kill renders this bait not as efficient as the baits of the present invention.

EXAMPLE 25-31

A series of baits prepared as in Example 2 are used to test the residual or egg kill of the bait of the present invention.

20 gravid female German roaches are placed in a tank with water, food, and a hide and given 24 hours to become acclimated. The bait is placed in the tray and mortality count is taken at 7 days for the roaches and the ootheca (egg capsules) are retained for 60 days and compared to an untreated control. The results are shown in Table VIII.

TABLE VIII

| Example | % Dursban Conc. | % Dog Chow | % Gravid Female Roaches Dead 7 Days | % Oothecae of Dead Roaches Hatched 60 Days |
|---|---|---|---|---|
| 25 | 0.25 | 69.5 | 85 | 0 |
| 26 | 0.35 | 69.5 | 90 | 5.5 |
| 27 | 0.50 | 69.5 | 85 | 5.9 |
| 28 | 0.75 | 69.5 | 90 | 0 |
| 29 | 1.00 | 69.5 | 100 | 4.8 |
| 30 | 1.25 | 69.5 | 90 | 5.5 |
| 31 | 1.50 | 69.5 | 90 | 0 |
| Control | 0 | 70.0 | 0 | 100* |

Paraffin - Balance of bait to 100%
*100% was reached in 30 days.

As is apparent, the baits of the present invention exhibit the surprising property of preventing hatch adding further to the effectiveness of the baits.

EXAMPLES 32–33

The bait of Example 1 is prepared and tested along with a similar bait having 20% of the dry dog food replaced with Maltose. These baits are tested on both American and German roaches. The results are shown in Table IX.

TABLE IX

| | | % Mortality (hours) | | | |
|---|---|---|---|---|---|
| Example | Roach | 4 | 8 | 24 | 32 |
| 32 | German | 80 | 95 | 98 | 99 |
| 32 | American | 0 | 26 | 89 | 100 |
| 33 | German | 98 | 100 | 100 | 100 |
| 33 | American | 0 | 50 | 100 | 100 |

EXAMPLE 34

The bait of Example 1 was tested against field infestation of German Roaches. The test areas were kitchens and baths, if adjacent to a kitchen. The population was counted by placing 6 to 12 traps around the site for 24 hours. Depending on the degree of infestation from 6 to 12 of 2.5–3.0 gram baits were placed. Additional trappings were taken at 2 to 3 week intervals to determine reduction in population. The results are shown in Table X.

TABLE X

| Test Site | # Trapped Initially | # Trapped | Effective Control % Reduction | # Weeks |
|---|---|---|---|---|
| A | 405 | 8 | 98 | 6 |
| B | 12 | 1 | 92 | 4 |
| C | 41 | 4 | 90 | 14 |

TABLE X-continued

| Test Site | # Trapped Initially | # Trapped | Effective Control % Reduction | # Weeks |
|---|---|---|---|---|
| D | 760 | 39 95 | 4 | |
| E | 78 | 6 | 92 | 4 |
| F | 26 | 1 | 96 | 4 |
| G | 219 | 101* | 54 | 4 |
| H | 45 | 2 | 96 | 4 |

*High trapping count due to baits being completely consumed sometime within 4 weeks. Additional baits must be placed to eradicate the final 50%.

EXAMPLES 35–40 and COMPARATIVE EXAMPLES 15–18

A series of non-toxicant baits were prepared using the attractants and waxes as shown in Table IX in a ratio of 70% attractant to 30% wax. These baits were observed for 20 days after which the amount of each bait consumed by the German roaches was measured.

TABLE XI

| Ex. | Wax | Attractant | # of Roaches on Bait in 48 hours | Mg. of Bait Consumed After 20 days |
|---|---|---|---|---|
| 35 | Beeswax | Purina Dog Chow | 12 | 70 |
| 36 | Paraffin | Purina Dog Chow | 26 | 441 |
| 37 | Beeswax | Brown Sugar | 8 | 68 |
| 38 | Paraffin | Brown Sugar | 21 | 236 |
| 39 | Beeswax | Maltose | 9 | 206 |
| 40 | Paraffin | Maltose | 5 | 127 |
| CE-15 | Beeswax | Potato Flakes | 1 | 43 |
| CE-16 | Paraffin | Potato Flakes | 1 | 16 |
| CE-17 | Beeswax | — | 4 | 0 |
| CE-18 | Paraffin | — | 9 | 0 |

As is apparent, the maltose, brown sugar, and dog chow are all more attractive to German roaches than the potato flakes previously used.

What is claimed is:

1. A bait composition comprising an intimate mixture of:
   a. from about 20 to 54.75% by weight of a non-repellent binder;
   b. from about 79.75 to 45% by weight of a food attractant selected from the group consisting of dry dog food, maltose, brown sugar, or mixtures thereof; and
   c. from about 0.25 to 5% by weight of 0,0-diethyl-0-(3,5,6-trichloro-2-pyridyl) phosphorothioate.

2. The bait of claim 1 wherein said binder is a waxy material.

3. the bait of claim 2 wherein said waxy material is a paraffin wax melting between 100°–250° F.

4. The bait of claim 2 wherein said waxy material is a natural wax.

5. The bait of claim 2 wherein said composition comprises from about 25 to 39.75% by weight binder, from about 79.75 to 55% by weight food attractant, and from about 0.25 to 3% by weight 0.0-diethyl-0-(3,5,6-trichloro-2-pyridyl) phosphorothioate.

6. The bait of claim 2 wherein said food attractant is dry dog food.

7. The bait of claim 2 wherein said food attractant is a mixture of dry dog food and maltose.

8. The bait of claim 5 wherein said composition comprises from about 24 to 34.5% by weight of a wax melting between 100-250° F., from about 65 to 75% by weight of food attractant, and from about 0.5 to 1% by weight of 0.0-diethyl-0-(3,5,6-trichloro -2-pyridyl) phosphorothioate.

9. The bait of claim 8 wherein said food attractant is dry dog food.

10. The bait of claim 9 wherein said wax is a paraffin wax.

* * * * *

UNITED STATES PATENT OFFICE
CERTIFICATE OF CORRECTION

Patent No. 4,049,460          Dated September 20, 1977

Inventor(s) David J. Broadbent

It is certified that error appears in the above-identified patent and that said Letters Patent are hereby corrected as shown below:

Column 3, line 47, "Lt" should be --LT--.

Column 8, Table X, line 5, under "# Trapped", delete "95"; under "% Reduction", delete "4" and insert --95--; and under "# Weeks", insert --4--.

Claim 3, line 1, "the" should be --The--.

Claim 5, line 4, "0.0" should be --0,0--.

Claim 8, line 5, "0.0" should be --0,0--.

Signed and Sealed this

Twentieth Day of December 1977

[SEAL]

Attest:

RUTH C. MASON        LUTRELLE F. PARKER
Attesting Officer      Acting Commissioner of Patents and Trademarks